(12) United States Patent
Van Tol et al.

(10) Patent No.: US 11,076,623 B2
(45) Date of Patent: *Aug. 3, 2021

(54) INTESTINAL BARRIER INTEGRITY

(71) Applicant: N.V. NUTRICIA, Zoetermeer (NL)

(72) Inventors: Eric Alexander Franciscus Van Tol, Arnhem (NL); Linette Eustachia Maria Willemsen, Driebergen-Rijsenburg (NL); Marleen Antoinette Koetsier, Epe (NL); Christopher Beermann, Petersberg (DE); Bernd Stahl, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/706,725

(22) Filed: Dec. 7, 2019

(65) Prior Publication Data
US 2020/0281241 A1    Sep. 10, 2020

Related U.S. Application Data

(63) Continuation of application No. 14/739,850, filed on Jun. 15, 2015, now Pat. No. 10,499,676, which is a continuation of application No. 13/594,147, filed on Aug. 24, 2012, now Pat. No. 9,084,433, which is a continuation of application No. 11/571,122, filed as application No. PCT/NL2004/000444 on Jun. 22, 2004, now Pat. No. 8,252,769.

(51) Int. Cl.
| | | |
|---|---|---|
| *A23L 29/00* | (2016.01) | |
| *A23L 33/00* | (2016.01) | |
| *A23L 33/12* | (2016.01) | |
| *A61K 31/202* | (2006.01) | |
| *A61K 31/702* | (2006.01) | |
| *A23L 29/30* | (2016.01) | |

(52) U.S. Cl.
CPC .............. *A23L 29/04* (2016.08); *A23L 29/30* (2016.08); *A23L 33/12* (2016.08); *A23L 33/40* (2016.08); *A61K 31/202* (2013.01); *A61K 31/702* (2013.01); *A23V 2002/00* (2013.01)

(58) Field of Classification Search
CPC .......... A23L 33/40; A23L 33/12; A23L 29/30; A23L 29/04; A23V 2002/00; A23V 2200/32; A23V 2200/304; A23V 2250/187; A23V 2250/1868; A23V 2250/1862; A23V 2250/28; A61K 31/702; A61P 37/08; A61P 1/00
USPC ......................................................... 514/54
See application file for complete search history.

(56) References Cited

U.S. PATENT DOCUMENTS

| | | |
|---|---|---|
| 2,981,629 A | 4/1961 | Ginnette et al. |
| 3,956,228 A | 5/1976 | Nogami et al. |
| 4,237,118 A | 12/1980 | Howard |
| 4,412,946 A | 11/1983 | Zalisz et al. |
| 4,438,147 A | 3/1984 | Hedrick, Jr. |
| 5,292,723 A | 3/1994 | Audry et al. |
| 5,374,657 A | 12/1994 | Kyle |
| 5,444,054 A | 8/1995 | Garleb et al. |
| 5,472,952 A | 12/1995 | Smidt et al. |
| 5,502,041 A | 3/1996 | Moen et al. |
| 5,531,988 A | 7/1996 | Paul |
| 5,629,023 A | 5/1997 | Bland |
| 5,629,040 A | 5/1997 | Takemori et al. |
| 5,709,888 A | 1/1998 | Gil et al. |
| 5,733,579 A | 3/1998 | Wolf et al. |
| 5,744,134 A | 4/1998 | Paul |
| 5,773,094 A | 6/1998 | Kruckel |
| 5,776,887 A | 7/1998 | Wibert et al. |
| 5,792,754 A | 8/1998 | Green et al. |
| 5,827,526 A | 10/1998 | Dohnalek et al. |
| 5,840,361 A | 11/1998 | Theuer et al. |
| 5,846,569 A | 12/1998 | Anderson et al. |
| 5,882,648 A | 3/1999 | Yoshihara et al. |
| 6,051,260 A | 4/2000 | Liska et al. |
| 6,197,758 B1 | 3/2001 | Ohtsuki et al. |
| 6,231,889 B1 | 5/2001 | Richardson et al. |
| 6,306,908 B1 | 10/2001 | Carlson et al. |
| 6,337,137 B1 | 1/2002 | Koldijk et al. |
| 6,426,110 B1 | 7/2002 | Basa |
| 6,451,584 B2 | 9/2002 | Tomita et al. |
| 6,468,987 B1 | 10/2002 | Demichele et al. |
| 6,576,251 B1 | 6/2003 | Stahl et al. |
| 6,632,445 B2 | 10/2003 | Richardson et al. |
| 6,645,543 B2 | 11/2003 | Gohman et al. |

(Continued)

FOREIGN PATENT DOCUMENTS

| | | |
|---|---|---|
| AU | 199728718 B2 | 7/1997 |
| CA | 2340103 | 2/2000 |

(Continued)

OTHER PUBLICATIONS 14.0 Spray Drying, obtained from http://class.fst.ohio-state.edu/Dairy_Tech/14Spraydrying.htm, Mar. 1, 2000, 15 pages.
Agostoni et al., "From nutrient composition to infants' function," Minerva Pediatrica, vol. 47, No. 3, 1995, pp. 181-194.
AIDS Fact Sheet: T-cell tests; also available at http://web.archive.org/web/20040217112225/http://www.aids.org/factSheets/124-T-Cell-Tests.html, published 2004; last viewed Oct. 21, 2009.
Alanate 385 Dispersible Calcium Caseinate, specification sheet, 2 pages, no date available (cited in US 2006-0110516, Office Action dated Mar. 1, 2010).

(Continued)

*Primary Examiner* — Ganapathy Krishnan
(74) *Attorney, Agent, or Firm* — N.V. Nederlandsch Octrooibureau; Catherine A. Shultz; Katelyn J. Bernier

(57) ABSTRACT

The invention concerns a method for stimulating barrier integrity in a mammal by administering to a mammal a composition comprising: eicosapentaenoic acid (EPA), docosahexaenoic acid (DHA) and arachidonic acid (ARA), and at least two distinct oligosaccharides.

20 Claims, 4 Drawing Sheets

(56) References Cited

U.S. PATENT DOCUMENTS

| | | | |
|---|---|---|---|
| 6,713,113 | B2 | 3/2004 | Bisperink et al. |
| 6,737,089 | B2 | 5/2004 | Wadsworth et al. |
| 6,794,495 | B1 | 9/2004 | Sorensen |
| 6,846,501 | B2 | 1/2005 | Prosise et al. |
| 6,872,416 | B2 | 3/2005 | Chmiel et al. |
| 6,974,841 | B1 | 12/2005 | Rapisarda |
| 7,351,715 | B2 | 4/2008 | Richardson et al. |
| 7,576,070 | B2 | 8/2009 | Kunz et al. |
| 7,601,364 | B2 | 10/2009 | Sawatzki et al. |
| 8,252,769 | B2 * | 8/2012 | van Tol .............. A23L 29/04 514/54 |
| 10,499,676 | B2 * | 12/2019 | Van Tol ............... A23L 33/40 |
| 2002/0015760 | A1 | 2/2002 | Prosise et al. |
| 2002/0016289 | A1 | 2/2002 | Conneely et al. |
| 2002/0018839 | A1 | 2/2002 | Chmiel et al. |
| 2002/0044988 | A1 | 4/2002 | Fuchs et al. |
| 2002/0127322 | A1 | 9/2002 | Bisperink et al. |
| 2002/0197313 | A1 | 12/2002 | Richardson et al. |
| 2003/0022863 | A1 | 1/2003 | Stahl et al. |
| 2003/0054083 | A1 | 3/2003 | Gohman et al. |
| 2003/0165604 | A1 | 9/2003 | Tsubaki et al. |
| 2004/0018996 | A1 | 1/2004 | Richardson et al. |
| 2004/0062758 | A1 | 4/2004 | Mayra-Makinen et al. |
| 2004/0072791 | A1 | 4/2004 | Kunz et al. |
| 2004/0122105 | A1 | 6/2004 | Bettle et al. |
| 2004/0219188 | A1 | 11/2004 | Comer et al. |
| 2006/0110516 | A1 | 5/2006 | Holtus et al. |
| 2007/0036839 | A1 | 2/2007 | Tuduri et al. |
| 2007/0098762 | A1 | 5/2007 | Stahl et al. |
| 2007/0110758 | A1 | 5/2007 | Campbell et al. |
| 2007/0166446 | A1 | 7/2007 | Boursier |
| 2008/0015166 | A1 | 1/2008 | Van Tol et al. |
| 2008/0064656 | A1 | 3/2008 | Van Tol |
| 2008/0138435 | A1 | 6/2008 | Van Den Berg et al. |
| 2008/0171720 | A1 | 7/2008 | Garssen et al. |
| 2008/0207559 | A1 | 8/2008 | Sawatzki et al. |
| 2009/0082249 | A1 | 3/2009 | Garssen et al. |
| 2010/0016214 | A1 | 1/2010 | Sawatzki et al. |
| 2010/0069320 | A1 | 3/2010 | Speelmans |
| 2010/0167982 | A1 | 7/2010 | Van Tol et al. |
| 2011/0077189 | A1 | 3/2011 | Vriesema |
| 2011/0236500 | A1 | 9/2011 | Van Den Berg et al. |

FOREIGN PATENT DOCUMENTS

| | | |
|---|---|---|
| DE | 10027050 A1 | 2/1957 |
| DE | 28 44 861 A1 | 4/1980 |
| DE | 37 34 962 C1 | 1/1989 |
| DE | 19940011 A1 | 3/2001 |
| DE | 10136260 A1 | 2/2003 |
| EP | 0 355 905 A1 | 2/1990 |
| EP | 0 378 824 | 7/1990 |
| EP | 0 378 824 B1 | 7/1990 |
| EP | 0 382 355 B1 | 8/1990 |
| EP | 0 484 266 A2 | 5/1992 |
| EP | 0 504 055 A1 | 9/1992 |
| EP | 0 511 761 A1 | 11/1992 |
| EP | 0 524 796 A1 | 1/1993 |
| EP | 0 307 523 B1 | 3/1993 |
| EP | 0 596 717 A1 | 5/1994 |
| EP | 0 615 752 A1 | 9/1994 |
| EP | 0 641 562 A1 | 3/1995 |
| EP | 0 692 252 A1 | 1/1996 |
| EP | 0 705 539 A2 | 4/1996 |
| EP | 0 711 503 A2 | 5/1996 |
| EP | 0 756 828 A1 | 2/1997 |
| EP | 0 593 774 B1 | 6/1997 |
| EP | 0 813 815 A1 | 12/1997 |
| EP | 0 745 330 B1 | 10/1998 |
| EP | 0 745 001 B1 | 11/1998 |
| EP | 0 756 828 B1 | 11/1998 |
| EP | 0 958 825 A1 | 11/1999 |
| EP | 1 074 181 A1 | 2/2001 |
| EP | 1 105 002 B1 | 6/2001 |
| EP | 0 631 731 B1 | 9/2001 |
| EP | 1 155 627 A1 | 11/2001 |
| EP | 1 228 694 A1 | 8/2002 |
| EP | 1 272 058 | 1/2003 |
| EP | 0 941 088 B1 | 3/2003 |
| EP | 1 321 527 | 6/2003 |
| EP | 1 321 527 A1 | 6/2003 |
| EP | 1 454 990 | 9/2004 |
| EP | 1 597 978 A1 | 11/2005 |
| EP | 1 454 990 B1 | 2/2006 |
| EP | 1 721 611 A1 | 11/2006 |
| EP | 1 723 951 A1 | 11/2006 |
| EP | 1 672 987 B1 | 5/2007 |
| EP | 1 815 755 B1 | 8/2007 |
| FR | 2781673 A1 | 2/2000 |
| FR | 2866203 A1 | 8/2005 |
| GB | 1 305 071 | 1/1973 |
| JP | 53-042340 A | 11/1978 |
| JP | 02-286058 A | 11/1990 |
| JP | 08-033448 A | 2/1996 |
| JP | 08-151328 A | 6/1996 |
| JP | 09-065855 A | 3/1997 |
| JP | 10-175867 A | 6/1998 |
| JP | 2003-146887 A | 5/2003 |
| JP | 2006-115826 | 5/2006 |
| NL | 1018832 C2 | 3/2003 |
| WO | WO-92/22588 A1 | 12/1992 |
| WO | WO-95/26646 A1 | 10/1995 |
| WO | WO-96/13271 A1 | 5/1996 |
| WO | WO-97/02829 A2 | 1/1997 |
| WO | WO-97/34615 A1 | 9/1997 |
| WO | WO-98/06276 A1 | 2/1998 |
| WO | WO-98/11910 A1 | 3/1998 |
| WO | WO-98/15196 A1 | 4/1998 |
| WO | WO-98/26787 A1 | 6/1998 |
| WO | WO-98/31241 A1 | 7/1998 |
| WO | WO-98/46764 A1 | 10/1998 |
| WO | WO-99/53777 A1 | 10/1999 |
| WO | WO-00/08948 A2 | 2/2000 |
| WO | WO-01/41581 A1 | 6/2001 |
| WO | WO-01/60378 A2 | 8/2001 |
| WO | WO-01/78530 A2 | 10/2001 |
| WO | WO-02/42484 A2 | 5/2002 |
| WO | WO-02/47612 | 6/2002 |
| WO | WO-02/47612 A2 | 6/2002 |
| WO | WO-02/060283 A2 | 8/2002 |
| WO | WO-02/076471 A1 | 10/2002 |
| WO | WO-03/093322 A2 | 11/2003 |
| WO | WO-03/102205 A1 | 12/2003 |
| WO | WO-2004/000042 A2 | 12/2003 |
| WO | WO-2004/000340 A2 | 12/2003 |
| WO | WO-2004/019699 A1 | 3/2004 |
| WO | WO-2004/026294 A1 | 4/2004 |
| WO | WO-2004/052121 A1 | 6/2004 |
| WO | WO-2004/112508 A1 | 12/2004 |
| WO | WO-2004/112509 A2 | 12/2004 |
| WO | WO-2004/113415 A1 | 12/2004 |
| WO | WO-2005/039319 A1 | 5/2005 |
| WO | WO-2005/039597 A2 | 5/2005 |
| WO | WO-2005/067955 | 7/2005 |
| WO | WO-2005/067955 A1 | 7/2005 |
| WO | WO-2005/110121 A1 | 11/2005 |
| WO | WO-2005/122790 A1 | 12/2005 |
| WO | WO-2006/007676 A1 | 1/2006 |
| WO | WO-2006/014519 A1 | 2/2006 |
| WO | WO-2006/112694 A2 | 10/2006 |
| WO | WO-2006/112716 A2 | 10/2006 |
| WO | WO-2006/112717 A2 | 10/2006 |
| WO | WO-2007/016132 A2 | 2/2007 |
| WO | WO-2007/115210 A2 | 10/2007 |
| WO | WO-2009/096772 A1 | 8/2009 |
| WO | WO-2009/096789 A1 | 8/2009 |

OTHER PUBLICATIONS

Alles et al., "Current trends in the composition of infant milk formulas," Current Paediatrics, vol. 14, 2004, pp. 51-63.

(56) References Cited

OTHER PUBLICATIONS

Alter et al., "Sequential deregulation of NK cell subset distribution and function starting in acute HIV-1 infection," Blood, vol. 106, No. 10, Nov. 15, 2005, pp. 3366-3369.
Analysis of RAFTIMIX 10; RAFTIMIX® ST and RAFTILOSE® P95, (1995).
Anonymous, "Larch Arabinogalactan," Alternative Medicine Review, vol. 5, No. 5, 2000, pp. 463-466.
Barcelo et al., "Mucin secretion is modulated by luminal factors in the isolated vascularly perfused rat colon," Gut, vol. 46, 2000, pp. 218-224.
Bedell, G. N. et al., J. Clin. Invest., Measurement of the Volume of Gas in the Gastrointestinal Tract. Values in Normal Subjects and Ambulatory Patients, Mar. 1956, vol. 35, No. 3, pp. 336-345.
Bernhart et al., "Lactulose in Modified Milk Products for Infant Nutrition," J. Dairy Sci., 1956, pp. 399-400.
Blaut, M. (2002) Relationship of prebiotics and food to intestinal microflora. European Journal of Nutrition, vol. 41, suppl. 1, pp. I/11-I16.
Boehm et al., "Prebiotics and Immune Responses," Journal of Pediatric Gastroenterology and Nutrition, vol. 39, Jun. 2004, pp. S772-S773.
Boehm et al., "Supplementation of a bovine milk formula with an oligosaccharide mixture increases counts of faecal bifidobacteria in preterm infants," Fetal & Neonatal, vol. 86, No. 3, May 2002, pp. F178-F181.
Boehm, "Prebiotic concept for infant nutrition," Acta Paediatrica Suppl., vol. 441, 2003, pp. 64-67.
Boersma et al., "Vitamin E, lipid fractions, and fatty acid composition of colostrum, transitional milk, and mature milk: an international comparative study," American Journal of Clinical Nutrition, Dep. of Obstetrics & Gynaecology, State Univ. Groningen, EZ Groningen 9713, Netherlands, vol. 3, No. 5, 1991, p. 1197-1204.
Bouhnik et al., "Administration of Transgalacto-Oligosaccharides Increases Fecal Bifiobacteria and Modifies Colonic Fermentation Metabolism in Healthy Humans," American Society for Nutritional Sciences, 1997 pp. 444-448.
Breitkreutz et al., "Improvement of immune functions in HIV infection by sulfur supplementation: Two randomized trials," Journal of Molecular Medicine (Berlin), vol. 78, No. 1, 2000, pp. 55-62.
Buckler, "Prebiotics in infant nutrition," Internet article online Jul. 8, 2001, pp. 1-5 (XP002292254), retrieved from the Internet: URL:http://ww.se-neonatal.es/se-neonatal/oviedo2001/prebiotics.pdf on Aug. 11, 2004.
Campbell et al., "An Enteral Formula Containing Fish Oil, Indigestible Oligosaccharides, Gum Arabic and Antioxidants Affects Plasma and Colonic Phospholipid Fatty Acid and Prostaglandin Profiles in Pigs," Journal of Nutrition, vol. 127, No. 1, Jan. 1997, pp. 137-145.
Caplan et al., "Effect of Polyunsaturated Fatty Acid (PUFA) Supplementation on Intestinal Inflammation and Necrotizing Enterocolitis (NEC) in a Neonatal Rat Model," Pediatric Research, vol. 49, No. 5, 2001, pp. 647-652.
Carlson et al., "Lower Incidence of Necrotizing Enterocolitis in Infants Fed a Preterm Formula with Egg Phospholipds," Pediatric Research, vol. 44, issue 4, Oct. 1998, pp. 491-498.
Carver et al., "The role of nucleotides in human nutrition," J. Nutr. Biochem., vol. 6, Feb. 1995, pp. 58-72.
Cho et al., Complex Carbohydrates in Foods, Marcel Dekker Inc., NY, 1999, pp. 229-233, 146 (ISBN: 0-8247-0187-9).
Claud et al., "Hypothesis: inappropriate colonization of the premature intestine can cause neonatal necrotizing enterocolitis," The FASEB Journal, vol. 15, Jun. 2001, pp. 1398-1403.
CODEX STAN 72, "Standard for Infant Formula and Formulas for Special Medical Purposes Intended for Infants," 1981, pp. 1-21.
Connor et al., "Increased Docosahexaenoic Acid Levels in Human Newborn Infants by Administration of Sardines and Fish Oil During Pregnancy," Lipids, vol. 31, Supplement, 1996, pp. S-183-S-187.
Craig et al., "Polydextrose as Soluble Fiber: Physiological and Analytical Aspects," American Assn of Cereal Chemists, Inc., vol. 43, No. 5, May 1998, pp. 370-376 (publication No. W-1998-0427-03F).
Crittenden et al, "Production, properties and applications of food-grade oligosaccharides," Trends in Food Science & Technologies, vol. 7, Nov. 1996, pp. 353-361.
Cummings, "Gastrointestinal Effects of Food Carbodhydrate.sup.1-3," Am J Clin Nutr, Apr. 1995; Suppl. 4 61 (suppl): pp. 938S-945S.
Dairy Chemistry and Physics, University of Guelph, obtained from http://www.foodsci.uoguelph.ca/dairyedu/chem.html, Feb. 4, 2001, 16 pages.
Database CA 'Online! Chemical Abstracts Service, Columbus, Oh, Nogami, "Resin Compositions for low-temperature curable powder paints," retrieved from STN Database accession No. 87:137415 abstract & JP 53 042340 B, Nov. 10, 1978.
Database Medline [Online], US NLM, Dec. 1994, Malorni et al.: "Thiol supplier N-acetylcysteine enhances conjugate formation between natural killer cells and K562 or U937 targets but increases the lytic function only against the latter," Database accession No. NLM7721335, & Immunology Letters, vol. 43, No. 3, Dec. 1994, 1 page [XP002474080].
Database WPI Week 199633, Derwent Publications, Ltd., London, GB: AN 1996-329426 [XP-002426042].
Database WPI, Section Ch, Week 200261, Derwent Publications Ltd., London, GB, Class A26, AN 2002-567199 & CN 1 343 727 A, Apr. 10, 2002 [XP-002344565].
Database WPI, Section Ch. Week 198929, Derwent Publications Ltd., London, GB, Class B03, AN 1989-211474.
Database WPI, Section Ch. Week 199615, Derwent Publications Ltd., London, GB, Class B04, AN 1996-145913.
Database WPI, Week 200634, Derwent Publications Ltd., London, GB, AN 2006-323978 & JP 2006 115826 A, May 2006 [XP-002474081].
Detry, Dissertation, 1992, Institute Paul Lambin "Implications technologiques et nutritionelles . . . ".
Dombo et al., "Production Health Benefits and Applications of Galacto-oligosaccharides," Yalpani M. ed., New Technologies for Healthy Foods and Neutraceuticals, ATL Press, Shewsbury, MA, 1997, pp. 143-156.
Dongowski et al., "The Degree of Methylation Influences the Degradation of Pectin in the Intestinal Tract of Rats In Vitro." The Journal of Nutrition, vol. 132, 2002, pp. 1935-1944.
Droege et al, "Is AIDS the consequence of a virus-induced cysteine and glutathione deficiency? Chances and limitations of the treatment with N-acetyl-cysteine (NAC)," AIDS Research and Human Retroviruses, vol. 10, no. Suppl. 3, 1994, p. S65 (XP008052583).
Droege et al., "Glutathione and immune function," Proceedings of the Nutrition Society, vol. 59, No. 4, Nov. 2000, pp. 595-600.
Droege et al., "Role of cysteine and glutathione in HIV infection and other diseases associated with muscle wasting and immunological dysfunction," FASEB Journal, vol. 11, No. 13, Nov. 1997, pp. 1077-1089.
Droege, "Cysteine and glutathione deficiency in AIDS patients: A rationale for the treatment with N-Acetyl-Cysteine," Pharmacology (Basel), vol. 46, No. 2, 1993, pp. 61-65.
Elfstrand et al., "Immunoglobulins, growth factors and growth hormone in bovine colostrum and the effects of processing," International Dairy Journal, vol. 12, 2002, pp. 879-887.
Elix'or® "Galacto-oligosaccharides for Innovative Foods," Borculo Whey Products product information material.
Elix'or® "Galacto-oligosaccharides: A natural ingredient for functional foods," Borculo Whey Products product information brochure, Jul. 1996.
European Partial Search Report dated Sep. 14, 2005, EP 05 10 3260, 5 pages.
European Partial Search Report dated Sep. 19, 2005, EP 1 723 951 A1, 5 pages.
Facchini et al., "Increased number of circulating Leu 11+ (CD 16) large granular lymphocytes and decreased NK activity during human ageing," Clinical Experimental Immunology, vol. 68, No. 2, 1987, pp. 340-347.

(56) References Cited

OTHER PUBLICATIONS

Fanaro et al., "Galacto-Oligosaccharides and Long-Chain Fructo-Oligosaccharides as Prebiotics in Infant Formulas: A Review," Acta Paediatrica Supplement, 94(449):22-26 (2005).
FAO Corporate Document, "The relationship between food composition and available energy," Provisional Agenda Item 4.1.3, Oct. 5-17, 1981, Rome, by D.A.T. Southgage, A.R.C. Food Research Institute, Norwich, UK, 10 pages.
Ferrandez et al., "Effects in vitro of several antioxidants on the natural killer function of aging mice—differing roles for IFN-gamma and IL-2," Experimental Gerontology, vol. 34, No. 5, Aug. 1999, pp. 675-685 [XP002474079].
FIBRULINE® Instant, Certificate of Analysis, Cosucra B.V., Netherlands, Oct. 12, 1994, 1 page.
Fidler et al., "Polyunsaturated fatty acid composition of human colostrum lipids in Slovenia: regional differences," Food Technology and Biotechnology, vol. 38, No. 2, 2000, pp. 149-153, Biotech. Fac., Inst. of Nutr., Univ. of Ljubljana, SI-1230 Domzale, Slovenia.
Fidler et al., "The fatty acid composition of human colostrum," European Journal of Nutrition, vol. 39, No. 1, Feb. 2000, pp. 31-37.
Fox, "Bovine Colostrum as a Resource for the Powerful Antioxicant Glutathione," Immune-Tree South Africa, Nov. 2008, pp. 1-7.
Frisomum, Analysis Chart and Brochure, 1998.
Ghoneum et al., "Enhancement of Natural Killer Cell Activity of Aged Mice by Modified Arabinoxylan Rice Bran (MGN-3/Biobran)," J. Pharm. and Pharmacology, vol. 56, No. 12, Dec. 2004, pp. 1581-1588.
Ghoneum et al., "Production of Tumor Necrosis Factor-Alpha and Interferon-Y from Human Peripheral Blood Lymphocytes by MGN-3, a Modified Arabinoxylan from Rice Bran, and Its Synergy with Interleukin-2 In Vitro," Cancer Detection and Prevention, vol. 24, No. 4, 2000, pp. 314-324.
Gibson et al., "Dietary Modulation of the Human Colonic Mlcrobiota: Introducing the Concept of Prebiotics," American Institute of Nutrition, 0022-3166, 1995, pp. 1401-1412.
Gibson et al., "Selective stimulation of bifidobacteria in the Human Colon by Oligofructose and Inulin," Gastroenterology, vol. 108, 1995, pp. 975-982.
Gibson, "Bifidogenic properties of different types of fructo-oligosaccharides," Food Microbiology, vol. 11, 1994, pp. 491-498.
Glade, Nutritional Pharmaceuticals "Conference Summary: First Symposium of the International College of Advanced Longevity Medicine, Reno, Nevada, Oct. 11-13, 1998," Nutrition, vol. 16, Issue 9, 2000, pp. 789-790.
Gonzalez et al., "Polysaccharides as Antiviral Agents: Antiviral Activity of Carrageenan," Antimicrobial Agents and Chemotherapy, vol. 31, No. 9, Sep. 1987, pp. 1388-1393.
Guggenbichler et al., "Acidic oligosaccharides from natural sources block adherence of *Escherichia coli* on uroepithelial cells," Pharm. Pharmacol. Lett., vol. 7, No. 1, Jun. 1997, pp. 35-38.
Haastrecht, "Oligosaccharides: Promising Performers in New Product Development," IFI, No. 1, 1995, pp. 23-27.
Hallert, C. et al. Scand. J. Gastroenterol., Ispaghula Husk May Relieve Gastrointestinal Symptoms in Ulcerative Colitis in Remission, 1991, vol. 26, No. 7, pp. 747-750.
Harmsen et al., "Analysis of Intestinal Flora Development in Breast-Fed and Formula-Fed Infants by Using Molecular Identification and Detection Methods," J. Pediatr. Gastroenterol. Nutr., vol. 30, 2000, pp. 61-67.
Hartemink "Non-digestible oligosaccharides: healthy food for the colon?," Proceedings of the International Symposium, Wageningen Pers, NL, Dec. 4-5, 1997, pp. 130-131 (ISBN 90-74134-52-1).
Hauer et al., "Mechanism of Stimulation of Human Natural Killer Cytotoxicity by Arabinogalactan from Laris Occidentalis," Cancer Immuno. Immunotherapy, vol. 36, No. 4, 1993, pp. 237-244.
Hendricks et al., "High-fiber diet in HIV-positive men is associated with lower risk of developing fat deposition"; Am J Clin Nutr, 2003; pp. 790-795.

Hertzler et al., "Colonic Adaptation to Daily Lactose Feeding in Lactose-Maldigesters Reduces Lactose-Intolerance," Am. J. Clin. Nutr., 1996, pp. 232-236.
Hirayama, "Novel physiological functions of oligosaccharides," Pure Appl. Chem., vol. 74, No. 7, 2002, pp. 1271-1279.
Hopkins et al., "Nondigestible Oligosaccharides Enhance Bacterial Colonization Resistance against Clostridium difficile In Vitro," Applied and Environmental Microbioloby, vol. 69, issue 4, Apr. 2003, pp. 1920-1927.
Igoe et al., Dictionary of Food Ingredients, 3rd Ed., Chapman and Hall, 1996, pp. 46, 66, 67, and 94.
Innovate with RAFTILINE® (ORAFTI Leaflet), Nov. 1996.
Innovate with RAFTILOSE RAFTIMIX® (ORAFTI leaflet), Nov. 1996.
International Search Report (PCT/NL2006/050091) dated Mar. 28, 2007.
International Search Report (PCT/NL2006/050092) dated Mar. 30, 2007.
International Search Report dated Mar. 28, 2007, PCT/NL2006/050091, 4 pages.
International Search Report dated Mar. 30, 2007, PCT/NL2006/050092, 4 pages.
International Search Report dated Sep. 24, 2004, PCT/NL2004/000451.
International Search Report for PCT/NL2004/000444, dated Mar. 3, 2005, 2 pages.
International Search Report, PCT/NL2005/000451, dated Feb. 8, 2006.
Isolauri et al., "Probiotics in the management of atopic eczema," Clinical and Experimental Allergy, vol. 30, 2000, pp. 1604-1610.
Ito et al., "Effects of Administration of Galactooligosaccharides on the Human Faecal Microflora, Stool Weight and Abdominal Sensation," Microbial Ecology in Health and Disease, vol. 3, No. 6, Nov.-Dec. 1990, pp. 285-292.
Ito et al., "Effects of Transgalactosylated Disaccharides on the Human Intestinal Microflora and Their Metabolism," J. Nutr. Sci. Vitaminol., vol. 39, 1993, pp. 279-288.
Ito et al., "Influence of Galactooligosaccharides on the Human Fecal Microflora," J. Nutr. Sci. Vltaminol, vol. 39, 1993, pp. 635-640.
Ito et al., "Influence of Lactose on Faecal Microflora in Lactose Maldigestors," Microbial Ecology in Health and Disease, vol. 6, 1993, pp. 73-76.
Jacobson et al., "Absolute or total lymphocyte count as a marker for the CD4 T lymphocyte criterion for initiating antiretroviral therapy," AIDS (Hagerstown), vol. 17, No. 6, Apr. 11, 2003, pp. 917-919 (XP008052430).
Jenkins et al., "Inulin, Oligofructose and Intestinal Function," J. Nutrition, vol. 129, 1999, pp. 1431S-1433S.
Jiang et al., "In Vitro Lactose Fermentation by Human Colonic Bacteria is Modified by Lactobacillus Acidophilus Supplementation," American Society for Nutritional Sciences, 1997, pp. 1489-1495.
Jirapinyo et al., "HIV Disease: Working Group Report of the First World Congress of Pediatric Gastroenterology, Hepatology, and Nutrition," J. Ped. Gastroenterology and Nutrition, vol. 35, Aug. 2002, pp. S134-S142.
Kirk-Othmer, Encyclopedia of Chemical Technology, 4th Ed., vol. 12, 1994, pp. 855-856.
Kleessen et al., "Fructans in the diet cause alterations of intestinal mucosal architecture, released mucins and mucosa-associated bifidobacteria in gnotobiotic rats," British Journal of Nutrition, vol. 89, 2003, pp. 597-606.
Klose et al., "Gums," CRC Handbook of Food Additives, Chpt. 7, 2nd Ed., 1972, pp. 305-307.
Kohmoto et al., "Effect of Isomalto-oligosaccharides on Human Fecal Flora," Bifidobacteria microflora, vol. 7, No. 2, 1988, pp. 61-69.
Koletzko et al., "Growth, development and differentiation: a functional food science approach," British Journal of Nutrition, vol. 80, Suppl. 1, 1998, pp. S5-S45.
Kulkarni et al., "Immunostimulant activity of inulin isolated from Saussurea lappa roots," Indian Journal of Pharmaceutical Sciences, vol. 63, No. 4, Jul. 2001, pp. 292-294.

(56) References Cited

OTHER PUBLICATIONS

Laidlaw et al., "Effects of supplementation with fish oil-derived n-3 fatty acids and (-linolenic acid on circulating plasma lipids and fatty acid profiles in women," Am J Clin Nutr, vol. 77, 2003, pp. 37-42.
Listing of sales of RAFTIMIX® 10 to clients i.a. in period Sep. 13, 1996 to May 19, 1998.
Manufacture protocol with composition of RAFTIMIX® 10 1995.

* cited by examiner

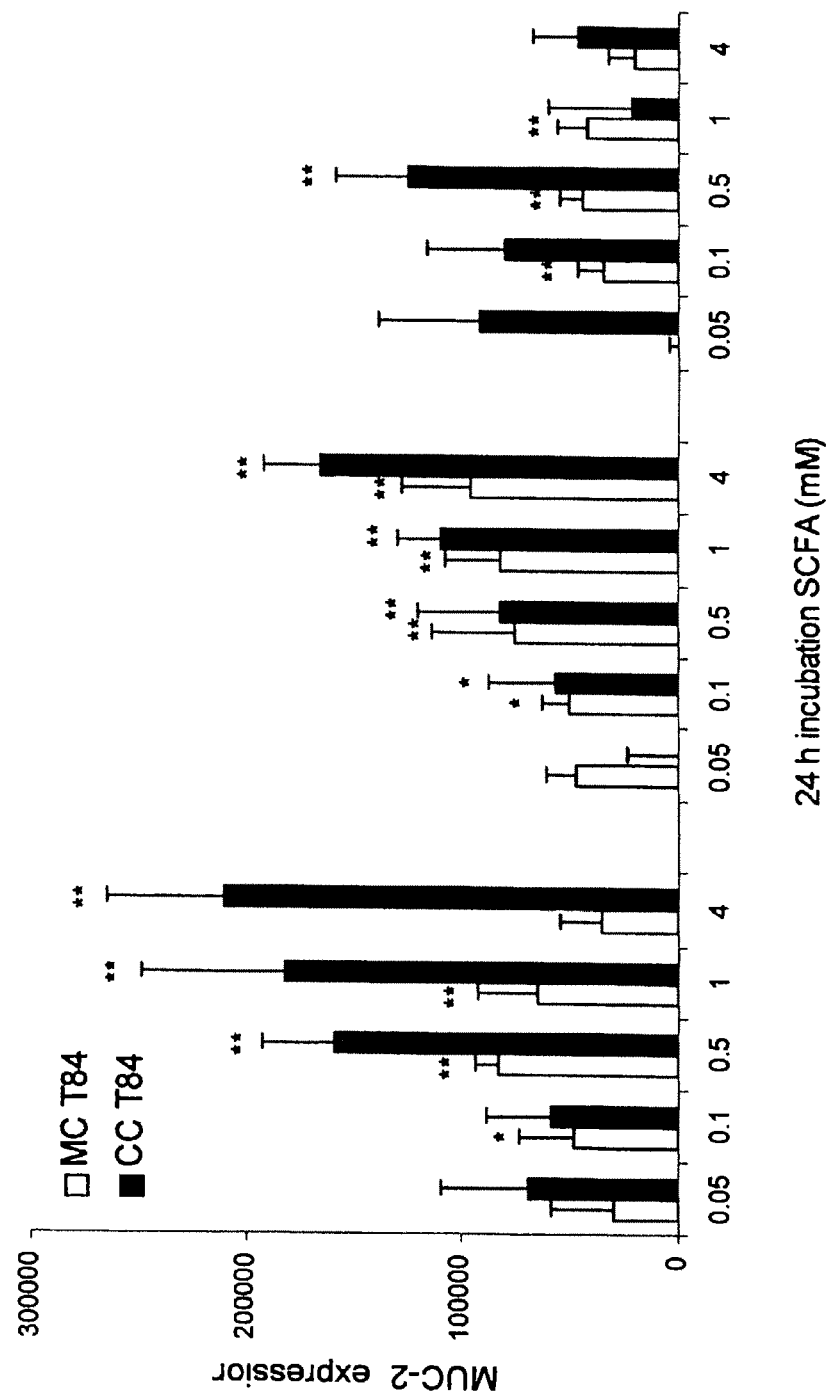

INTESTINAL BARRIER INTEGRITY

CROSS-REFERENCE TO RELATED APPLICATIONS

This application is a Continuation of U.S. application Ser. No. 14/739,850, filed Jun. 15, 2015, which is a Continuation of U.S. application Ser. No. 13/594,147, filed Aug. 24, 2012, which is a Continuation of U.S. application Ser. No. 11/571,122, filed Sep. 6, 2007, which is a National Stage entry of International Application No. PCT/NL2004/000444, filed Jun. 22, 2004, the entire contents of which are hereby incorporated by reference.

FIELD OF THE INVENTION

The present invention relates to a method for improving intestinal barrier integrity and a composition suitable for use in such method.

BACKGROUND OF THE INVENTION

The gastrointestinal epithelium normally functions as a selective barrier permitting the absorption of nutrients, electrolytes and water and preventing the exposure to dietary and microbial antigens, including food allergens. The gastrointestinal epithelium limits the passage of antigens to the systemic circulation, that may be causing inflammatory reactions, e.g. allergic reactions. As the incidence of allergy, particularly food allergy, is increasing, many research groups search for (preventive) cures for these ailments.

EP1272058 describes a composition containing indigestible oligosaccharides for improving tight junction to reduce intestinal permeability and reducing allergic reaction. The composition may comprise LC-PUFA's (long chain-polyunsaturated fatty acids).

EP 745001 describes a combination of indigestible oligosaccharides and n-3 and n-6 fatty acids for treatment ulcerative colitis.

Usami et al (Clinical Nutrition 2001, 20(4): 351-359) describe the effect of eicosapentaenoic acid (EPA) on tight junction permeability in intestinal monolayer cells. In their hands, EPA was found to increase permeability, indicating that EPA is unsuitable to improve intestinal barrier integrity.

The prior art formulations are not optimally suited for improving barrier integrity.

SUMMARY OF THE INVENTION

The present invention provides a combination of selected long chain polyunsaturated fatty acids (LC-PUFA's) and selected oligosaccharides. The present combination of LC-PUFA's and oligosaccharides effectively improves barrier integrity, by synergistically improving intestinal permeability and mucus production, and is particularly suitable for improving barrier integrity in human infants.

It was surprisingly found that selected LC-PUFA's effectively reduce epithelial paracellular permeability. In contrast to what Usami et al (Clinical Nutrition 2001, 20(4): 351-359) have reported, the present inventors found that C18 and C20 polyunsaturated fatty acids, particularly eicosapentaenoic acid (EPA), docosahexaenoic acid (DHA) and arachidonic acid (ARA), are capable of effectively reducing intestinal tight junction permeability.

In addition to the LC-PUFAs, the present composition contains oligosaccharides. The selected oligosaccharides improve the barrier integrity by stimulating the production of the mucus, which results in an increased mucus layer thickness. It is believed this effect is caused by the effects of the distinct oligosaccharides on the short chain fatty acid (SCFA) production. Hence, when enterally administered to a mammal, the present combination of LC-PUFA and indigestible oligosaccharides synergistically improve barrier integrity and/or synergistically reduce intestinal permeability by simultaneous reduction of tight junction permeability and stimulation of mucus production.

In a further aspect, the present composition improves the quality of the intestinal mucus layer. The mucus layer comprises mucins. Mucins are high molecular mass glycoproteins that are synthesized and secreted by goblet cells. They form a gel-like layer on the mucosal surface, thereby improving barrier integrity. The mucus layer comprises different types of mucins, e.g. acid, neutral and sulphonated mucins. An increased heterogeneity of the mucus layer is believed to improve barrier functionality.

The present composition preferably comprises at least two different oligosaccharides, which influence the mucosal architecture and advantageously influence mucin heterogeneity in the mucus layer, either directly or by changing the intestinal flora. Each different selected oligosaccharide is believed to have a different effect on mucus quantity and quality. Moreover, the two distinct oligosaccharides are also able to stimulate quality of mucus as reflected by the degree of sulphation through their synergistic stimulation of SCFA production. It was surprisingly found by the present inventors that a mixture of two different oligosaccharides according to the present invention synergistically stimulates acetate production. It was also found by the present inventors mucus production is dependent on acetate production.

The present composition is preferably further improved by providing both long- and short-chain oligosaccharides. The supply of different chain lengths results in stimulation of mucus production in different parts of the ileum and colon. The short chain oligosaccharides (typically with a degree of polymerisation (DP) of 2,3,4 or 5) stimulate mucin production in the proximal colon and/or distal ileum, while the oligosaccharides with longer chain lengths (preferably with a degree of polymerisation (DP) of more than 5 up to 60) are believed to stimulate mucin production in the more distal parts of the colon.

Even further improvements can be achieved by providing the at least two different oligosaccharides both as short-chain and long-chain oligosaccharides. These preferred embodiments all contribute to further improved barrier integrity throughout the ileum and/or colon.

Furthermore, it was surprisingly found that EPA, DHA and ARA were able to reduce the harmful effects of interleukin 4 (IL-4) on intestinal permeability. IL-4 is a cytokine which is secreted in increased amounts by mucosal T-cells in certain patients and induces intestinal permeability. Hence the present invention also provides for a method for the treatment and/or prevention of diseases wherein intestinal IL-4 concentration is increased, such as allergy, particularly atopic dermatitis.

BRIEF DESCRIPTION OF THE DRAWINGS

FIG. 4 shows the differential effects of SCFA (acetate, proprionate, butyrate) on MUC-2 expression in intestinal epithelial cells (MC T84) and epithelial-mesenchymal cell co-cultures (CC T84).

DETAILED DESCRIPTION OF THE INVENTION

Figure 1A:
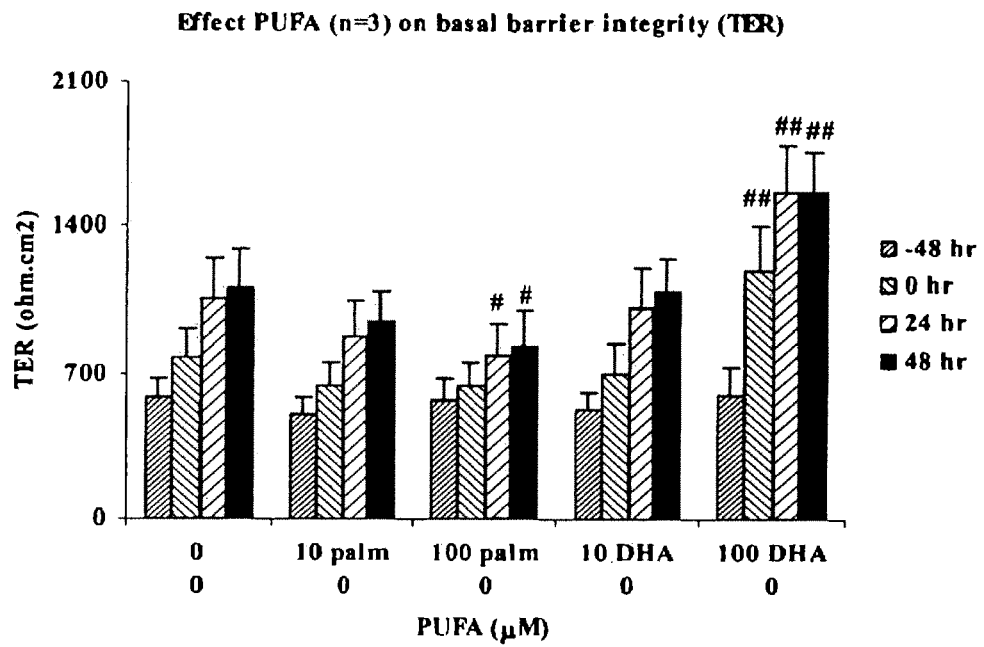
FIGS. 1A and 1B show the time and dose dependent effects of palmitic acid and DHA (FIG. 1A) and GLA and AA (FIG. 1B) on basal barrier integrity (TER).

The present invention relates to a nutritional composition comprising:
a) EPA, DHA and ARA, wherein the content of long chain polyunsaturated fatty acid with 20 and 22 carbon atoms does not exceed 15 wt. % of the total fat content; and
b) at least two distinct oligosaccharides, wherein the two distinct oligosaccharides have a homology in monose units below 90%.

This composition can be advantageously used in a method for stimulating intestinal barrier integrity, said method comprising administering to a mammal said composition.
Polyunsaturated Fatty Acids The present inventors surprisingly found that eicosapentaenoic acid (EPA, n-3), docosahexaenoic acid (DHA, n-3) and arachidonic acid (ARA, n-6) effectively reduce intestinal tight junction permeability. Hence the present composition, which is particularly suitable for improving intestinal barrier integrity, comprises EPA, DHA and ARA.

The present inventors found that lower concentration of LC-PUFA's, were effective in reducing tight junction permeability (see Examples vs. Usami et al). Hence, the content of LC-PUFA with 20 and 22 carbon atoms in the present composition, preferably does not exceed 15 wt. % of the total fat content, preferably does not exceed 10 wt. %, even more preferably does not exceed 5 wt. % of the total fat content. Preferably the present composition comprises at least 0.1 wt. %, preferably at least 0.25 wt, more preferably at least 0.5 wt. %, even more preferably at least 0.75 wt. % LC-PUFA with 20 and 22 carbon atoms of the total fat content. For the same reason, the EPA content preferably does not exceed 5 wt. % of the total fat, more preferably does not exceed 1 wt. %, but is preferably at least 0.05 wt %, more preferably at least 0.1 wt. % of the total fat. The DHA content preferably does not exceed 5 wt. %, more preferably does not exceed I wt. %, but is at least 0.1 wt % of the total fat. As ARA was found to be particularly effective in reducing tight junction permeability, the present composition comprises relatively high amounts, preferably at least 0.1 wt. %, even more preferably at least 0.25 wt. %, most preferably at least 0.5 wt. % of the total fat. The ARA content preferably does not exceed 5 wt. %, more preferably does not exceed 1 wt. % of the total fat. In the present ARA containing enteral composition, EPA and DHA are advantageously added to balance the action of ARA, e.g. reduce the potential proinflammatory action of ARA metabolites. Excess metabolites from ARA may cause inflammation. Hence, the present composition preferably comprises ARA, EPA and DHA, wherein the weight ratio ARA/DHA preferably is above 0.25, preferably above 0.5, even more preferably above 1. The ratio is preferably below 25. The weight ratio ARA/EPA is preferably between 1 and 100, more preferably between 5 and 20.

The present composition preferably comprises between 5 and 75 wt. % polyunsaturated fatty acids based on total fat, preferably between 10 and 50 wt. %.

If the present composition is used as an infant formula (e.g. a method for feeding an infant, said method comprising administering the present composition to an infant), the content of LC-PUFA, particularly the LC-PUFA with 20 and 22 carbon atoms, preferably does not exceed 3 wt. % of the total fat content as it is desirable to mimic human milk as closely as possible. For the same reason, the omega-3 LC-PUFA content preferably does not exceed 1 wt. % of the total fat content; the omega-6 LC-PUFA content preferably does not exceed 2 wt. % of the total fat content; the ARA (omega-6) content is preferably below 1 wt. % of the total fat content; and/or the weight ratio EPA/DHA is preferably 1 or lower, more preferably below 0.5.

The LC-PUFA with 20 and 22 carbon atoms may be provided as free fatty acids, in triglyceride form, in phospholipid form, or as a mixture of one of more of the above. The present composition preferably comprises at least one of ARA and DHA in phospholipid form.

The present nutritional composition preferably also provides omega-9 (n-9) fatty acid (preferably oleic acid, 18:1), to provide sufficient nutrition. Preferably the present composition provides at least 15 wt. % n-9 fatty acid based on the weight of the total fatty acids, more preferably at least 25 wt %. The content of n-9 fatty acids is preferably below 80 wt. %.
Oligosaccharides Suitable oligosaccharides according to the invention are saccharides which have a degree of polymerisation (DP) of at least 2 monose units, which are not or only partially digested in the intestine by the action of acids or digestive enzymes present in the human upper digestive tract (small intestine and stomach), but which are fermentable by the human intestinal flora. The term monose units refers to units having a closed ring structure, preferably hexose, e.g. the pyranose or furanose forms. The degree of polymerisation of the oligosaccharide is typically below 60 monose units, preferably below 40, even more preferably below 20.

The present composition comprises at least two different oligosaccharides, wherein the oligosaccharides have a homology in monose units below about 90%, preferably below 50%, even more preferably below 25%, even more preferably below 5%. The term "homology" as used in the present invention is the cumulative of the percentage of same monose units in the different oligosaccharides. For example, oligosaccharide 1 (OL1) has the structure fruc-fruct-glu-gal, and thus comprises 50% fruc, 25% gal and 25% glu. Oligosaccharide 2 (OL2) has the structure fruc-fruc-glu, and thus comprises 66% fruc, 33% glu. The different oligosaccharides thus have a homology of 75% (50% fruc+25% glu).

In a preferred embodiment, the present composition comprises galactooligosaccharides and at least one selected from the group consisting of fructooligosaccharides and inulin.

Each of the present oligosaccharides preferably comprises at least 66%, more preferably at least 90% monose units selected from the group consisting of mannose, arabinose, fructose, fucose, rhamnose, galactose, β-D-galactopyranose, ribose, glucose, xylose, uronic acid and derivatives thereof, calculated on the total number of monose units contained therein.

According to a further embodiment at least one of the oligosaccharides of the present composition is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides, acidic oligosaccharides (see below, e.g. uronic acid oligosaccharides such as pectin hydrolysate) and mixtures thereof. Preferably the present composition comprises at least one, preferably at least two, of the oligosaccharides selected from the group consisting of fructooligosaccharides or inulin, galactooligosaccharides and pectin hydrolysate.

For good mucus quantity and quality, the present composition preferably comprises at least one oligosaccharide, which comprises at least 66% galatose or fructose as a monose unit. In a preferred embodiment the composition comprises at least one oligosaccharide which comprises at least 66% galatose as a monose unit and at least one oligosaccharide which comprises at least 66% fructose as a monose unit. In a particularly preferred embodiment, the present composition comprises galactooligosaccharide and an oligosaccharide selected from the group consisting of fructooligosaccharides and inulin. Fructooligosaccharides stimulate sulfomucin production in the distal colon of human flora-associated rats (Kleessen et al, (2003) Brit J Nutr 89:597-606) and galactooligosaccharides stimulate the acid mucin production (Meslin et al, Brit. J. Nutr (1993), 69: 903-912)).

For further improvement of mucus layer thickness over the whole area of the colon, at least 10 wt. % of the oligosaccharides in the present composition has a DP of 2 to 5 (i.e. 2, 3, 4 and/or 5) and at least 5 wt. % has a DP of 10 to 60. Preferably at least 50 wt. %, more preferably at least 75 wt. % of the oligosaccharides have a DP of 2 to 9 (i.e. 2, 3, 4, 5, 6, 7, 8, and/or 9), because these are believed to work throughout the ileum and proximal and middle parts of the colon and because the weight percentage of oligosaccharides that needs to be incorporated in the composition to achieve the desired effect is reduced.

Preferably the weight ratios:
a. (oligosaccharides with DP 2 to 5):(oligosaccharides with DP 6,7,8 and/or 9)>1; and
b. (oligosaccharides with DP 10 to 60):(oligosaccharides with DP 6,7,8 and/or 9)>1 are both above 1.

Preferably both weight ratios are above 2, even more preferably above 5.

For even further improvement of mucus layer thickness and quality over the whole area of the colon, preferably each of the at least two different oligosaccharides are provided in different chain lengths, preferably at least 10 wt. % of each oligosaccharide based on the total weight of the respective oligosaccharide has a DP of 2 to 5 (i.e. 2, 3, 4 and/or 5) and at least 5 wt. % has a DP between 10 and 60. Preferably at least 50 wt. %, more preferably at least 75 wt. % of the oligosaccharide based on the total weight of that oligosaccharides has a DP between 2 and 10, because these are believed to work throughout in the ileum and proximal and middle parts of the colon.

Acidic Oligosaccharides

To further improve barrier integrity, the present composition preferably includes acidic oligosaccharides with a DP between 2 and 60. The term acid oligosaccharide refers to oligosaccharides comprising at least one acidic group selected from the group consisting of N-acetylneuraminic acid, N-glycoloylneuraminic acid, free or esterified carboxylic acid, sulfuric acid group and phosphoric acid group. The acidic oligosaccharide preferably comprises uronic acid units (i.e. uronic acid polymer), more preferably galacturonic acid units. The acid oligosaccharide may be a homogeneous or heterogeneous carbohydrate. Suitable examples are hydrolysates of pectin and/or alginate. In the intestinal tract, the uronic acid polymers are hydrolysed to uronic acid monomers, which stimulate production of intestinal acetate, which in turn stimulates intestinal mucus secretion (Barcelo et al., Gut 2000; 46:218-224).

Preferably the acid oligosaccharide has the structure I below, wherein the terminal hexose (left) preferably comprises a double bond. The hexose units other than the terminal hexose unit(s) are preferably uronic acid units, even more preferably galacturonic acid units. The carboxylic acid groups on these units may be free or (partly) esterified, and preferably at least 10% is methylated (see below).

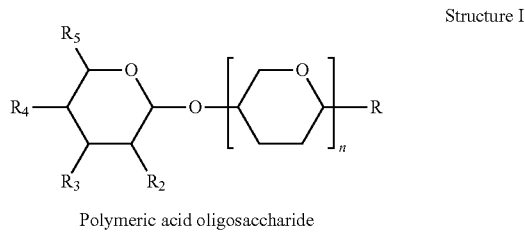

Structure I

Polymeric acid oligosaccharide wherein:
R is preferably selected from the group consisting of hydrogen, hydroxy or acid group, preferably hydroxy; and
at least one selected from the group consisting of $R_2$, $R_3$, $R_4$ and $R_5$ represents N-acetylneuraminic acid, N-glycoloylneuraminic acid, free or esterified carboxylic acid, sulfuric acid group and phosphoric acid group, and the remaining of $R_2$, $R_3$, $R_4$ and $R_5$ representing hydroxy and/or hydrogen. Preferably one selected from the group consisting of $R_2$, $R_3$, $R_4$ and $R_5$ represents N-acetylneuraminic acid, N-glycoloylneuraminic acid, free or esterified carboxylic acid, sulfuric acid group or phosphoric acid group, and the remaining represent hydroxy and/or hydrogen. Even more preferably one selected from the group consisting of $R_2$, $R_3$, $R_4$ and $R_5$ represents free or esterified carboxylic acid and the remaining of $R_2$, $R_3$, $R_4$ and $R_5$ representing hydroxy and/or hydrogen; and
n is an integer and refers to a number of hexose units (see also Degree of Polymerisation, below), which may be any hexose unit. Suitably n is an integer between 1-5000. Preferably the hexose unit(s) is a uronic acid unit.

Most preferably $R_1$, $R_2$ and $R_3$ represent hydroxy, $R_4$ represent hydrogen, $R_5$ represents carboxylic acid, n is any number between 1 and 250, preferably between 1 and 10 and the hexose unit is galacturonic acid.

The detection, measurement and analyses of the preferred acid oligosaccharides as used in the present method are given in applicants earlier patent application relating to acid oligosaccharides, i.e. WO 0/160378.

For stimulation improvement of mucus layer thickness over the whole area of the colon, the present composition preferably comprises at least 10 wt. % acid oligosaccharides with a DP of 2 to 5 (i.e. 2, 3, 4 and/or 5) and at least 5 wt. % acid oligosaccharides with a DP between 10 and 60, said wt. % being based on the total weight of the oligosaccharides.

The acid oligosaccharides used in the invention are preferably prepared from pectin, pectate, alginate, chondroitine, hyaluronic acids, heparine, heparane, bacterial carbohydrates, sialoglycans, fucoidan, fucooligosaccharides or carrageenan, more preferably from pectin and/or alginate.

Content of Oligosaccharide

When in ready-to-feed liquid form, the present composition preferably comprises 0.1 to 100 grams indigestible oligosaccharide per liter, more preferably between 0.5 and 50 grams per liter even more preferably between 1 and 25 grams per liter. A too high content of oligosaccharides may cause discomfort due to excessive fermentation, while a very low content may result in an insufficient mucus layer.

The weight ratio of the at least two different oligosaccharides is preferably between 1 and 10, more preferably between 1 and 5. These weight ratios stimulate mucin production of different types at different sites in the intestine optimally.

The oligosaccharide is preferably included in the present composition according to the invention in an amount exceeding 0.1 wt. %, preferably exceeding 0.2 wt. %, more preferably exceeding 0.5 wt. % and even more preferably exceeding 1 wt. % based on the total dry weight of the composition. The present composition preferably has an oligosaccharide content below 20-wt. %, more preferably below 10-wt. % even more preferably below 5-wt. %.

Addition of nucleotides and/or nucleosides to the present composition further improves gut mucosal barrier function, particularly as it inhibits and/or or reduces the incidence of bacterial translocation and decreases intestinal injury. Hence, the present composition preferably also comprises between 1 and 500 mg nucleosides and/or nucleotides per 100 gram of the dry formula, even more preferably between 5 and 100 mg.

Application

The present composition can be advantageously used in a method for improving barrier integrity in mammals, particularly humans. The present composition can also be advantageously used in a method for the treatment or prevention of diseases associated with reduced barrier integrity, said method comprising administering to a mammal the present composition. The present composition is preferably administered orally.

For the ill and infants, the present composition is preferably combined with complete nutrition, including protein, carbohydrate and fat. The present composition is advantageously administered to infants with the age between 0 and 2 years. The composition may be administered to patients which suffer from an impaired barrier integrity and healthy patients. The present composition is advantageously used in a method for providing the nutritional requirements of a premature infant (an infant born before 37 weeks gestation).

The present composition can also be advantageously used in a method for treatment and/or prevention of intestinal damage by administering the present composition to the patient prior to or after a medical treatment, which may cause intestinal damage. Such medical treatment may for example be surgery or enteral medicine treatment (e.g. antibiotic, analgesic, NSAID, chemotherapeutic agents etc).

The present composition can also be advantageously used to treat or prevent diseases wherein intestinal barrier disruption is underlying the development of the course of the disease, e.g. in a method for the treatment or prevention of chronic inflammatory diseases, particularly inflammatory bowel disease (IBD), irritable bowel syndrome (IBS), celiac disease, pancreatitis, hepatitis, arthritis or diabetes. Furthermore, the invention can be used in a method for providing nutrition to patients which have undergone or are undergoing abdominal surgery and patients that experience postoperative dysfunction of the gut and/or malnourished patients.

In a further embodiment of the invention the present composition is advantageously administered to patients suffering from acquired immune deficiency syndrome (AIDS) and/or patients which are infected with the human immunodeficiency virus (HIV), e.g. in a method for the treatment of AIDS and/or HIV infection. Said method comprises the oral administration of the present composition, preferably combined with nutrients selected from the group consisting of carbohydrate, protein and fat.

Furthermore, the invention can also be used to treat or prevent complications resulting from reduced barrier integrity, particularly in a method for the treatment and/or prevention of diarrhea, particularly infant diarrhea. Due to the reduced incidence in infant diarrhea, the present composition can also be advantageously used to reduce diaper rash.

Administering the present composition reduces passage of dietary and microbial antigens, particularly food allergens, from the intestinal lumen into the mucosa] or systemic circulation, and hence can be advantageously used in a method for the treatment or prevention of allergy and/or allergic reaction, particularly in a method for the treatment or prevention of food allergy, e.g. allergic reaction resulting from the ingestion of foodstuff.

It was also found by the present inventors that EPA, DHA and/or ARA are capable of reducing the effects of IL-4 on intestinal permeability. Hence, one aspect of the present invention provides for a method for the treatment and/or prevention of diseases wherein intestinal IL-4 concentration is increased (e.g. allergic diseases), said method comprising administering an LC-PUFA preferably selected from the group consisting of EPA, DHA and ARA, preferably combined with the present selected oligosaccharides. Hence, the present composition can also be advantageously used in a method for the treatment of atopic dermatitis.

Since the barrier function of newborns has not been fully developed, the present composition can be advantageously administered to young infants, i.e. infants with the age between 0 and 6 months. The composition may be administered to the infant in the form of an infant formula without human milk or admixed with human milk. Hence the present invention also provides for a formula feed comprising human milk and the present composition. The compositions including human milk and the present composition are particularly suitable for feeding premature infants.

The present composition is preferably provided as a packaged powder or packaged ready-to-feed formula. To prevent spoilage of the product, packaging size of ready-to-feed formula preferably does not exceed one serving, e.g. preferably does not exceed 500 ml; and packaging size of the present composition in powder form preferably does not exceed 250 servings. Suitable packaging sizes for the powder are 2000 grams or less, preferably per 1000 grams or less.

The packaged products provided with labels that explicitly or implicitly direct the consumer towards the use of said product in accordance with one or more of the above or below purposes, are encompassed by the present invention. Such labels may for example make reference to the present method for preventing allergic reaction to food allergens by including wording like "reduced food sensitivity", "improving intestinal tolerability", "improved food tolerance" or similar wording. Similarly, reference to the present method for treating and/or preventing allergy may be made by incorporating terminology equivalent to "improved resistance" or "reduced sensitivity".

Formula's

It was found that the present composition can be advantageously applied in food, such as baby food and clinical food. Such food preferably comprises lipid, protein and carbohydrate and is preferably administered in liquid form. The term "liquid food" as used in the present invention includes dry food (e.g. powders) which are accompanied with instructions as to admix said dry food mixture with a suitable liquid (e.g. water).

Hence, the present invention also relates to a nutritional composition which preferably comprises between 5 and 50 en % lipid, between 5 and 50 en % protein, between 15 and 90 en % carbohydrate and the present combination of oligosaccharides and LC-PUFA's. Preferably the present nutritional composition preferably contains between 10 and 30 en % lipid, between 7.5 and 40 en % protein and between 25 and 75 en % carbohydrate (en % is short for energy percentage and represents the relative amount each constituent contributes to the total caloric value of the preparation).

Preferably a combination of vegetable lipids and at least one oil selected from the group consisting of fish oil and omega-3 vegetable, algae or bacterial oil is used.

The proteins used in the nutritional preparation are preferably selected from the group of non-human animal proteins (such as milk proteins, meat proteins and egg proteins), vegetable proteins (such as soy protein, wheat protein, rice protein, and pea protein), free amino acids and mixtures thereof. Cow milk derived nitrogen source, particularly cow milk protein proteins such as casein and whey proteins are particularly preferred.

A source of digestible carbohydrate may be added to the nutritional formula. It preferably provides about 40% to about 80% of the energy of the nutritional composition. Any suitable (source of) carbohydrate may be used, for example sucrose, lactose, glucose, fructose, corn syrup solids, and maltodextrins, and mixtures thereof.

The present composition is preferably used as an infant formula and preferably contains 7.5 to 12.5 energy % protein; 40 to 55 energy % carbohydrates; and 35 to 50 energy % fat. As the present composition is suitably used to reduce the allergic reaction in an infant, the protein of the infant formula is preferably selected from the group consisting of hydrolyzed milk protein (e.g. hydrolyzed casein or hydrolyzed whey protein), vegetable protein and/or amino acids. The use of these proteins further reduced the allergic reactions of the infant.

Stool irregularities (e.g. hard stools, insufficient stool volume, diarrhea) is a major problem in many babies and ill subjects that receive liquid foods. It was found that stool problems may be reduced by administering the present oligosaccharides in liquid food which have an osmolality between 50 and 500 mOsm/kg, more preferably between 100 and 400 mOsm/kg.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

EXAMPLES

Example 1: Effect of LC-PUFA on Barrier Integrity

Monolayers (MC) of intestinal epithelial cell lines T84 (American Type Culture Collection (ATTC), Manassas, USA) were cultured on transwell filters (Corning, Costar BV, The Netherlands) allowing both mucosal and serosal sampling and stimulation of human intestinal epithelial cells. Two weeks post confluency the monolayers were incubated in the luminal compartment with polyunsaturated fatty acids ARA (arachidonic acid; 5,8,11,14-eicosatetraenoic acid), DHA (cis-4,7,10,13,16,19 docosahexaenoic acid), EPA (eicosapentaenoic acid) or control palmitic (C 16:0) acid (Palm) (Sigma, St. Louis, USA). The latter procedure was chosen to mimic the in vivo administration route of the dietary compounds. Cells were incubated with ARA, DHA, EPA, or palmitic acid for 0, 24, 48 and 72 hr at different concentrations (10 µM and 100 µM). Experiments were performed to evaluate basal barrier integrity. The epithelial barrier function was determined by measuring the transepithelial resistance (TER, $\Omega \cdot cm^2$) was measured by epithelial volt-ohm meter (EVOM; World Precision Instruments, Germany) and permeability for 4 kD FITC dextran (paracellular permeability marker, Sigma, USA). Resistance (Epithelial permeability for 4 kDa FITC-dextran was determined as follows. Prior to dextran fluxes the medium was refreshed with culture medium without phenol red for one hour followed by addition of 5 µl (stock 100 mg/ml) 4 kDa FITC-dextran to the lumenal compartment. After 30 min incubation 100 µl sample was collected from the serosal compartment and the fluorescent signal measured at excitation wavelength 485 nm and emission 520 nm (FLUOstar Galaxy®, BMG Labtechnologies, USA). FITC-dextran fluxes were calculated as pmol FITC-dextran/$cm^2$/h. Statistical analyses were performed using the ANOVA (SPSS version 10).

Results of the effect of fatty acids (100 µM) on spontaneous barrier integrity after 72 hr incubation are given in Table 1. Table 1 shows that the LC-PUFA's ARA, EPA and DHA reduce the molecular flux and improve epithelial resistance. In contrast the control experiments show that palmitic acid has the opposite effects, i.e. compromises barrier integrity. These results are indicative for the advantageous use of EPA, DHA and ARA, and in particularly ARA in the composition according to the present invention and for use in a method according to the present invention, e.g. in a method for improving barrier integrity. These result further support the synergistic effects of the present combination of fatty acids and indigestible oligosaccharides.

Figure 1B:
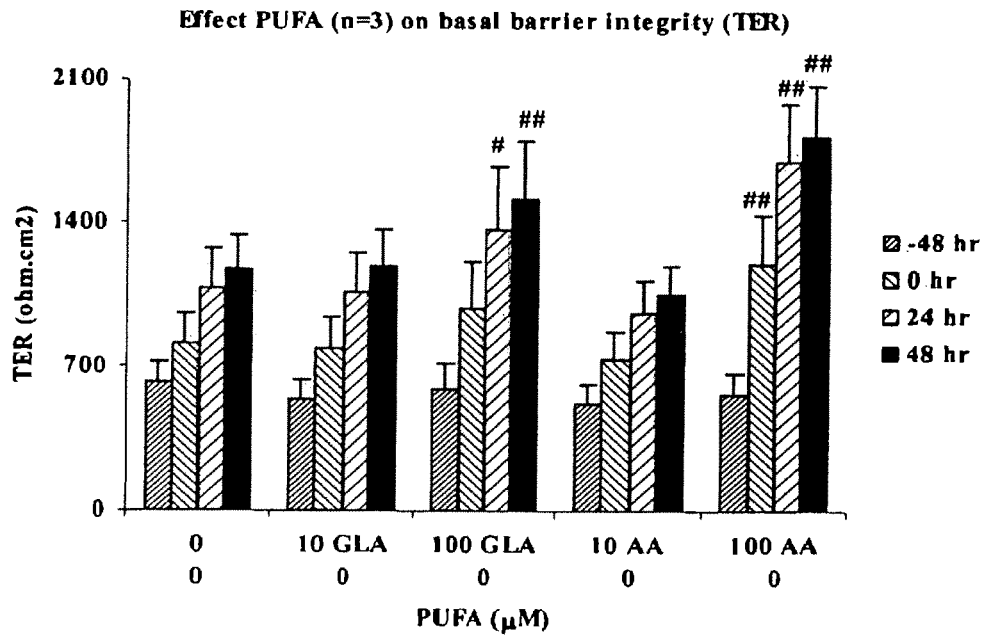

FIG. 1 shows the time and dose (10 µM and 100 µM) dependent effects of various fatty acids (palmitic acid, DHA, GLA, and AA) on basal barrier integrity (TER). FIG. 1 shows that the LC-PUFA's AA, DHA, and GLA, improve the epithelial barrier integrity as reflected by increased resistance (TER). These results are indicative for the advantageous use of EPA, DHA, GLA and ARA, in particularly ARA, in the composition according to the present invention and for use in a method according to the present invention, i.e. in a method for improving barrier integrity. These results further support the synergistic effects of the present combination of fatty acids and indigestible oligosaccharides.

TABLE 1

| Ingredient (LC-PUFA) | Flux | Resistance (TER) |
| --- | --- | --- |
| Control | 79 | 1090 |
| Palmitic acid | 161 | 831 |
| DHA | 72 | 1574 |
| ARA | 28 | 1816 |
| EPA | 65 | 1493 |

Example 2: Effect of LC-PUFA on IL-4 Mediated Barrier Disruption

Monolayers (MC) of intestinal epithelial cell lines T84 (ATCC, USA) were cultured on transwell filters (Corning, Costar BV, The Netherlands) allowing both mucosal and serosal sampling and stimulation of human intestinal epithelial cells. Two weeks post confluency the monolayers were incubated in the presence of IL-4 (2 ng/ml, serosal compartment, Sigma, USA) with or without polyunsaturated fatty acids ARA, DHA, GLA, EPA, or control palmitic acid (10 μM or 100 μM, mucosal compartment, Sigma, St. Louis, USA). Cells were pre-incubated with ARA, DHA, EPA, or palmitic acid for 48 hr prior to the IL-4 incubation. The co-incubation of PUFA's and palmetic acid with IL-4 was continued for another 48 hr; while culture medium and additives were changed every 24 hr. The epithelial barrier function was determined by measuring the transepithelial resistance (TER) and permeability as described in example 1. Statistical evaluation was performed as described in example 1.

Results of the effect of ARA, DHA, EPA and palmitic acid (100 μM) on IL-4 mediated barrier disruption are given in Table 2. Table 2 shows that the LC-PUFA's ARA, DHA and EPA inhibit the increased flux caused by IL-4. In contrast palmetic acid had a detrimental effect and decreased barrier disruption compared to control. These results are indicative for the advantageous use of ARA, DHA, and EPA in clinical and infant nutrition formulations to prevent or reduce IL-4 mediated barrier disruption, e.g. as occurs in food or cows milk allergy. These result further support the synergistic effects of the present combination of fatty acids and indigestible oligosaccharides.

Figure 2A:
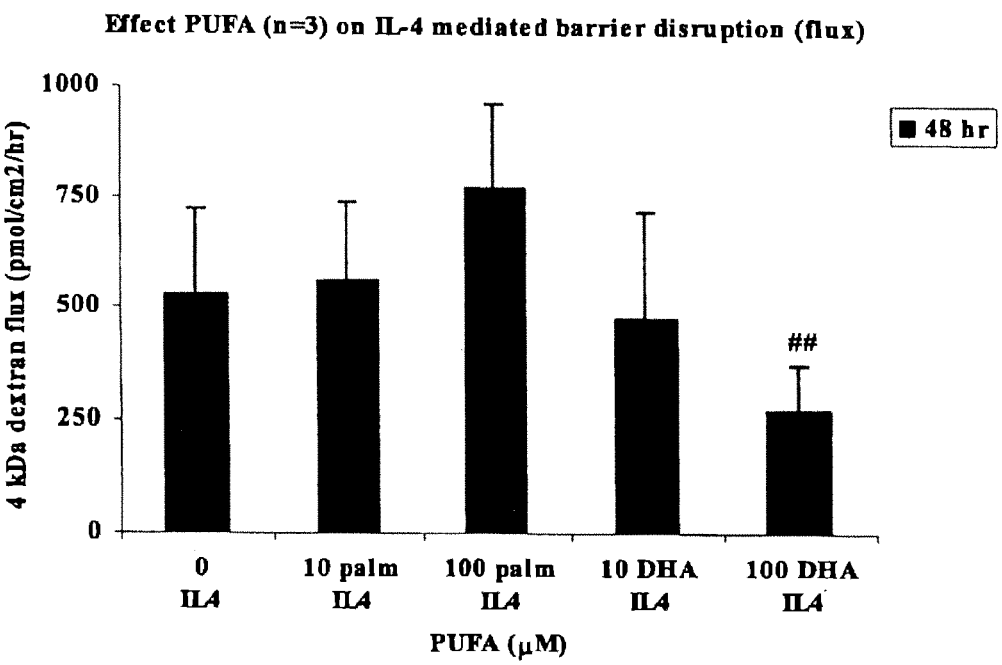
FIGS. 2A and 2B give the time and dose dependent protective effects of palmitic acid and DHA (FIG. 2A) and GLA and AA (FIG. 2B) on IL-4 mediated barrier destruction (Flux).
Figure 2B:
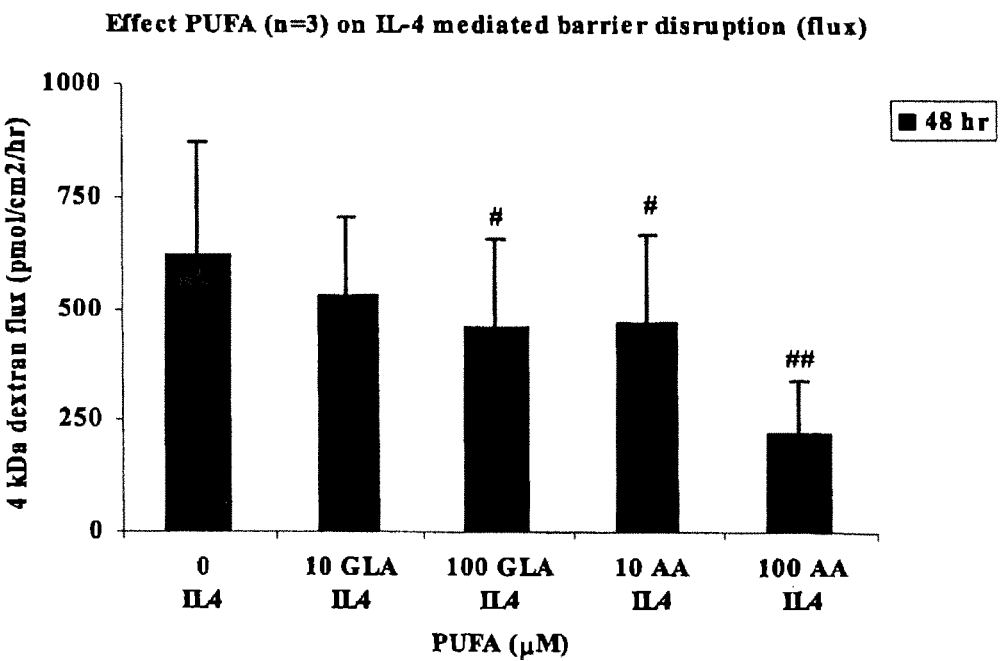

FIG. 2 gives the time and dose (10 μM and 100 μM) dependent protective effects of various FA's (palmitic acid, DHA, GLA, and AA) on IL-4 mediated barrier destruction (Flux). FIG. 2 shows that ARA, DHA and GLA protect against IL-4 mediated barrier disruption as reflected by decreased 4 kD dextran flux. These results are indicative for the advantageous use of ARA, DHA and GLA in clinical and infant nutrition formulations to prevent or reduce IL-4 mediated barrier disruption, e.g. as occurs in food or cows milk allergy. These result further support the synergistic effects of the present combination of fatty acids and indigestible oligosaccharides.

TABLE 2

| Ingredient (LC-PUFA) | IL-4 Flux | IL-4 TER |
| --- | --- | --- |
| Control | 582 | 374 |
| Palmitic acid | 777 | 321 |
| DHA | 271 | 547 |
| ARA | 218 | 636 |
| EPA | 228 | 539 |

Example 3: Effect of Oligosaccharides on Acetate Production

Micro-organisms were obtained from fresh faeces from bottle fed babies. Fresh faecal material from babies ranging 1 to 4 month of age was pooled and put into preservative medium within 2 h. As substrate either prebiotics (TOS; TOS/inulin (HP) mixture in a 9/1 (w/w) ratio; inulin; oligofructose(OS)/inulin mixture in a 1/1 (w/w) ratio, or none (blanc) were used. The transgalactooligosaccharides (TOS) were obtained from Vivinal GOS, Borculo Domo Ingredients, Zwolle, The Netherlands and comprises as indigestible oligosaccharides: 33 wt. % disaccharides, 39 wt. % trisaccharides, 18 wt. % tetrasaccharides, 7 wt. % pentasaccharides and 3 wt. % hexa-, hepta- en octasaccharides. The inulin (HP) Orafti active food ingredients, Tienen, Belgium, i.e. Raftiline HP®, with an average DP of 23. Media: McBain & MacFarlane medium: buffered peptone water 3.0 g/l, yeast extract 2.5 g/l. mucin (brush borders) 0.8 g/l, tryptone 3.0 g/l, L-Cysteine-HCl 0.4 g/l, bile salts 0.05 g/l, K2HPO4.3H2O 2.6 g/l, NaHCO$_3$0.2 g/l, NaCl 4.5 g/l, MgSO4.7H2O 0.5 g/l, CaCl2 0.228 g/l, FeSO4.7H2O 0.005 g/l. Fill 500 ml Scott bottles with the medium and sterilized 15 minutes at 121° C. Buffered medium: K2HPO4.3H2) 2.6 g/l, NaHCO$_3$0.2 g/l, NaCl 4.5 g/l, MgSO4.7H2O, 0.5 g/l, CaCl2 0.228 g/l, FeSO4.7H2O 0.005 g/l. Adjust to pH 6.3±0.1 with K2HPO4 or NaHCO$_3$. Fill 500 ml Scott bottles with the medium and sterilized 15 minutes at 121° C.

Preservative medium: Buffered peptone 20.0 g/l, L-Cysteine-HCl 0.5 g/l, Sodium thioglycollate 0.5 g/l, resazurine tablet 1 per litre, adjust to pH 6.7±0.1 with 1 M NaOH or HCl. Boiled in microwave. Serum bottles were filled with 25 ml medium and sterilized for 15 minutes at 121° C.

Fresh faecal samples were mixed with preservative medium and stored for several hours at 4° C. The preserved solution of faeces was centrifuged at 13,000 rpm for 15 minutes, supernatant removed and faeces mixed with McBain & Mac Farlane medium in a weight ratio of 1:5. Of this faecal suspension 3 ml were combined with 85 mg glucose or prebiotic or with no addition (blanc) in a bottle and mixed thoroughly. A t=0 sample was withdrawn (0.5 ml). 2.5 ml of the resulting suspension is brought in a dialysis tube in a 60 ml bottle filled with 60 ml of the buffered medium. The bottle was closed well and incubated at 37° C. Samples were taken from the dialysis tube (0.2 ml) or dialysis buffer (1.0 ml) with a hypodermic syringe after 3, 24, and 48 hours and immediately put it on ice to stop fermentation. The experiment was carried out using the following samples:
1) 85 mg TOS
2) 85 mg inulin
3) 85 mg TOS/inulin in a ratio of 9/1 (w/w) and
4) 85 mg OS/inulin in a ratio of 1/1 (w/w).

SCFA (acetate, propionate, butyrate) were quantitated using a Varian 3800 gas chromatograph (GC) (Varian Inc., Walnut Creek, U.S.A.) equipped with a flame ionisation detector. 0.5 μl of the sample was injected at 80° C. in the column (Stabilwax, 15×0.53 mm, film thickness 1.00 μm, Restek Co., U.S.A.) using helium as a carrier gas (3.0 psi). After injection of the sample, the oven was heated to 160° C. at a speed of 16° C./min, followed by heating to 220° C. at a speed of 20° C./min and finally maintained at 220° C. for 1.5 minutes. The temperature of the injector and detector was 200° C. 2-ethylbytyric acid was used as an internal standard.

Figure 3A:
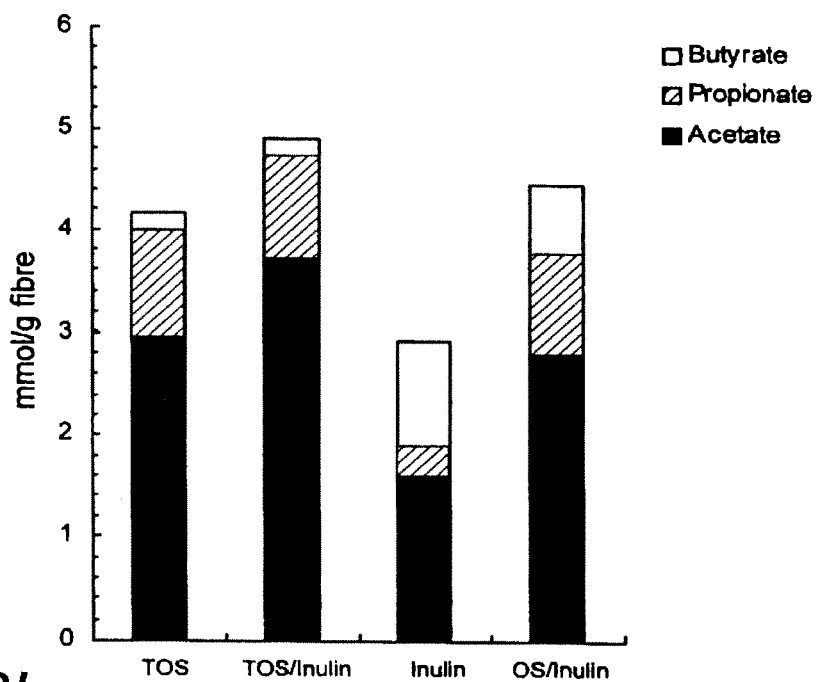
FIGS. 3A and 3B depict the absolute (FIG. 3A) and relative SCFA profile (FIG. 3B) resulting from fermenting the different oligosaccharides.
Figure 3B:
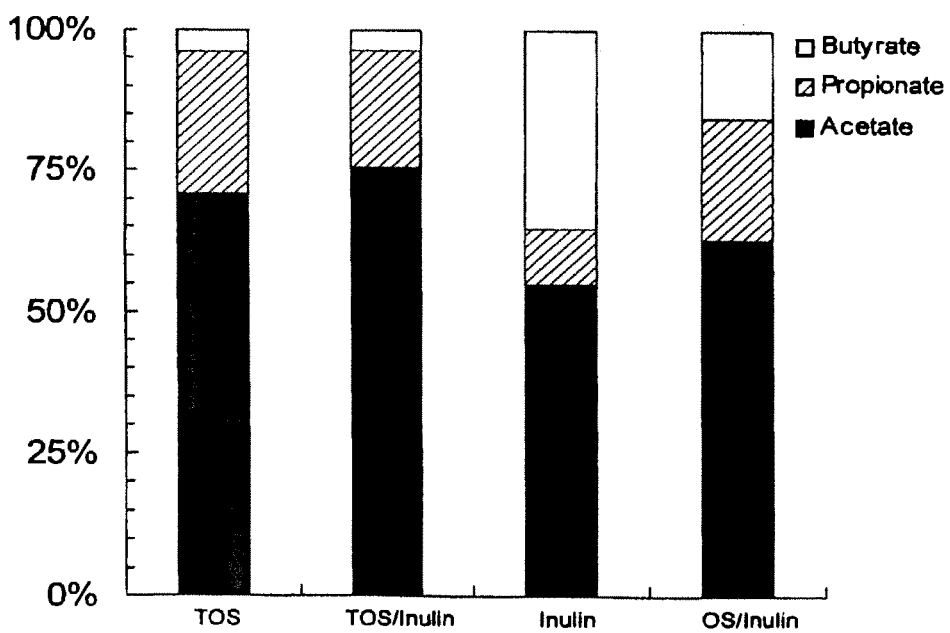

FIG. 3 depicts the absolute (FIG. 3A) and relative SCFA profile (FIG. 3B) resulting from fermenting the different oligosaccharides. FIG. 3A shows that a mixture of two different oligosaccharides (TOS/Inulin), wherein the two distinct oligosaccharides have a homology in monose units below 90 and a different chain length results in a significantly and synergistically increased amount of SCFA (particularly acetate) per gram fiber than single components. FIG. 3B shows that the addition of a combination of TOS/Inulin favored a higher proportion of the beneficial acetate (B). The acetate production in vivo translates to improved mucus production by goblet cells and a measure for intestinal mucus layer thickness (see example 4). These results are indicative for the advantageous use of the present composition.

Example 4: Effects of SCFA on Mucus Production

Monolayers of intestinal epithelial T84 cells (ATCC, USA) cells were cultured in 24 or 96 wells tissue culture plates (Corning B.V.). T84 were incubated with the short chain fatty acids acetate, proprionate and butyrate (SCFA, Merck, USA) for 24 h in a concentration range of 0.025-4.0 mM. Supernatants and/or cells were collected and MUC-2 (mucin) expression determined. A dotblot technique was used to determine MUC-2 expression in the cell cultures, since mucins are extremely large glycoproteins (over 500 kDa) which makes them difficult to handle in western blotting techniques. The method was validated using pre-immune serum (T84 stained negative), CCD-18Co (ATCC, USA) negative control cells and bovine serum albumin (BSA). Cell samples were collected in Laemmli (protein isolation buffer) and protein determination performed using a microprotein assay (Biorad, USA) according to the manufacturers protocol. Samples (0.3-0.7-1.0 μg/2 μl) were dotted on nitrocellulose membranes (Schleicher & Schuell, Germany). Membranes were blocked in TBST/5% Protivar (Nutricia, The Netherlands) followed by 1 h incubation with anti-MUC-2 antibody (kindly donated by Dr. Einerhand, Erasmus University, Rotterdam, The Netherlands). After washing, blots were incubated with goat anti-rabbit-HRP (Santacruz Biotechnology, USA) and for substrate detection ECL (Roche Diagnostics, The Netherlands) was used. Densitometry was performed using the Lumi-Imager (Boehringer Mannheim B. V., The Netherlands) and the signal was expressed in light units (BLU). BLU's were also expressed relative to control incubations (% BLU). To compare the stimulatory effect of SCFA on MUC-2 expression basal MUC-2 expression levels were deducted.

FIG. 4 shows the differential effects of SCFA (acetate, proprionate, butyrate) on MUC-2 expression in intestinal epithelial cells (MC T84) and epithelial-mesenchymal cell co-cultures (CC T84). FIG. 2 also shows that acetate is more potent in stimulating MUC-2 expression (mucus production) as compared to propionate and butyrate. Hence, the present combination of oligosaccharides (which was shown to increase acetate production (see example 3)) is particularly useful for stimulating mucus production and can be advantageously used in a method for stimulating barrier integrity.

Example 5: Infant Milk Formula I

Ingredients (per liter), energy 672 Kcal; Protein 15 g; Whey:Casein ratio 60:40; Fat 36 g; Carbohydrate 72 g; Vitamin A 750 RE; Mixed natural carotids 400 IU; Vitamin D 10.6 mcg; Vitamin F 7.4 mg; Vitamin K 67.0 mcg; Vitamin B.sub.1 (thiamin) 1000 mcg; Vitamin B.sub.2 (riboflavin) 1500 mcg; Vitamin B.sub.6 (pyridoxine) 600 mcg; Vitamin B.sub.12 (cyanacobalmine) 2.0 mcg; Niacin 9.0 mcg; Folic Acid 80 mcg; Pantothenic Acid 3000 mcg; Biotin 90 mcg; Vitamin C (ascorbic acid) 90 mg; Choline 100 mg; Inositol 33 mg; Calcium 460 Mg; Phosphorous 333 Mg; Magnesium 64 Mg; Iron 8.0 Mg; Zinc 6.0 Mg; Manganese 50 mcg; Copper 560 mcg; Iodine 100 mcg; Sodium 160 mg; Potassium 650 mg; Chloride 433 mg and Selenium 14 mcg; wherein the fat content provides includes 3 gram fish oil and 3 grams 40% arachidonic acid oil (DSM Food Specialties, Delft, Netherlands); further comprising 4 gram transgalactooligosaccharides Elix'or™ (Borculo Domo Ingredients, Netherlands) and 4 gram Raftiline™ (Orafti Active Food Ingredients, Belgium).

The invention claimed is:

1. A method for treating allergy, comprising administering to a subject in need thereof a nutritional composition comprising:
   (a) eicosapentaenoic acid (EPA) and arachidonic acid (ARA), wherein the content of long chain polyunsaturated fatty acid with 20 and 22 carbon atoms does not exceed 15 wt. % of the total fat content; and
   (b) at least two distinct oligosaccharides with a degree of polymerisation (DP) between 2 and 60 comprising transgalactooligosaccharide (TOS) and inulin.

2. The method according to claim 1, wherein at least 10 wt. % of the oligosaccharides has a degree of polymerisation (DP) between 2 to 5 and at least 5 wt. % of the oligosaccharides has a DP between 10 and 60.

3. The method according to claim 1, wherein the composition further comprises an acidic oligosaccharide with a DP between 2 and 60.

4. The method according to claim 3, wherein the acidic oligosaccharide is an uronic acid polymer with a DP between 2 and 6.

5. The method according to claim 1, wherein the composition further comprises DHA.

6. The method according to claim 1, wherein the composition comprises 7.5 to 12.5 energy % protein; 40 to 55 energy % carbohydrates; and 35 to 50 energy % fat, wherein said protein comprises hydrolyzed milk protein, vegetable protein, amino acids, or combinations thereof.

7. The method according to claim 1, wherein the composition comprises a caloric content of 0.6 to 0.8 kcal/ml; an osmolality of 50 to 500 mOsm/kg; and a viscosity below 50 mPas.

8. The method according to claim 1, wherein:
   (a) the content of long chain polyunsaturated fatty acid is below 3 wt. % of the total fat content;
   (b) the content of omega-3 long chain polyunsaturated fatty acid is below 1 wt. % of the total fat content; and
   (c) the content of omega-6 long chain polyunsaturated fatty acid is below 2 wt. % of the total fat content.

9. The method according to claim 1, wherein the composition further comprises between 5 and 100 mg nucleosides and/or nucleotides per 100 gram dry formula.

10. The method according to claim 1, wherein the composition is an infant formula.

11. A method for stimulating intestinal barrier integrity comprising administering to a subject in need thereof, a nutritional composition comprising:
    (a) eicosapentaenoic acid (EPA) and arachidonic acid (ARA), wherein the content of long chain polyunsaturated fatty acid with 20 and 22 carbon atoms does not exceed 15 wt. % of the total fat content; and
    (b) at least two distinct oligosaccharides with a degree of polymerisation (DP) between 2 and 60 comprising transgalactooligosaccharide (TOS) and inulin.

12. The method according to claim 11, wherein at least 10 wt. % of the oligosaccharides has a degree of polymerisation (DP) between 2 to 5 and at least 5 wt. % of the oligosaccharides has a DP between 10 and 60.

13. The method according to claim 11, wherein the composition further comprises an acidic oligosaccharide with a DP between 2 and 60.

14. The method according to claim 13, wherein the acidic oligosaccharide is an uronic acid polymer with a DP between 2 and 6.

15. The method according to claim 11, wherein the composition further comprises DHA.

16. The method according to claim 11, wherein the composition comprises 7.5 to 12.5 energy % protein; 40 to 55 energy % carbohydrates; and 35 to 50 energy % fat, wherein said protein comprises hydrolyzed milk protein, vegetable protein, amino acids, or combinations thereof.

17. The method according to claim 11, wherein the composition comprises a caloric content of 0.6 to 0.8 kcal/ml; an osmolality of 50 to 500 mOsm/kg; and a viscosity below 50 mPas.

18. The method according to claim 11, wherein:
(a) the content of long chain polyunsaturated fatty acid is below 3 wt. % of the total fat content;
(b) the content of omega-3 long chain polyunsaturated fatty acid is below 1 wt. % of the total fat content; and
(c) the content of omega-6 long chain polyunsaturated fatty acid is below 2 wt. % of the total fat content.

19. The method according to claim 11, wherein the composition further comprises between 5 and 100 mg nucleosides and/or nucleotides per 100 gram dry formula.

20. The method according to claim 11, wherein the composition is an infant formula.

\* \* \* \* \*